(12) United States Patent
Lee et al.

(10) Patent No.: US 7,708,905 B2
(45) Date of Patent: May 4, 2010

(54) METHOD FOR PREPARING ESTER COMPOUNDS AS BLEACH ACTIVATORS

(75) Inventors: Chang-Woo Lee, Daejeon (KR); Wan-Goo Cho, Daejeon (KR); Jin-Young Hyun, Daejeon (KR); Kyung-Hee Oh, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 214 days.

(21) Appl. No.: 10/594,804

(22) PCT Filed: May 25, 2004

(86) PCT No.: PCT/KR2004/001243

§ 371 (c)(1), (2), (4) Date: Oct. 17, 2008

(87) PCT Pub. No.: WO2005/095323

PCT Pub. Date: Oct. 13, 2005

(65) Prior Publication Data

US 2009/0105495 A1   Apr. 23, 2009

(30) Foreign Application Priority Data

Mar. 31, 2004   (KR) .................. 10-2004-0022434

(51) Int. Cl.
*C11D 3/39* (2006.01)
*C11D 7/54* (2006.01)

(52) U.S. Cl. .................. 252/186.38; 510/312; 510/309; 510/313; 510/314; 554/151; 558/372

(58) Field of Classification Search .................. 554/151, 554/95, 121; 510/309, 312, 313, 314; 252/186.38; 558/372

See application file for complete search history.

(56) References Cited

U.S. PATENT DOCUMENTS

| 4,179,390 A | 12/1979 | Spadini et al. |
| 4,259,201 A | 3/1981 | Cockrell, Jr. et al. |
| 4,412,934 A | 11/1983 | Chung et al. |
| 4,483,778 A | 11/1984 | Thompson et al. |
| 4,606,838 A | 8/1986 | Burns |
| 4,671,891 A | 6/1987 | Hartman |
| 4,686,061 A | 8/1987 | Nollet et al. |
| 5,043,089 A | 8/1991 | Nollet et al. |
| 5,098,598 A | 3/1992 | Sankey et al. |
| 5,520,844 A | 5/1996 | Venturello et al. |
| 5,575,947 A | 11/1996 | Venturello et al. |
| 5,705,091 A * | 1/1998 | Steichen et al. ........ 252/186.38 |

FOREIGN PATENT DOCUMENTS

| EP | 0 210 674 | 2/1987 |
| EP | 256443 | 2/1988 |
| EP | 396341 | 11/1990 |
| JP | 08 120295 | 5/1995 |
| WO | WO 2005/100530 | 10/2005 |

OTHER PUBLICATIONS

Neissner, R., 1978, "Preparation, analysis and TLC separation of partial esters of fatty acids with polyvalent alcohols", *Fette, Seifen, Anstichmittel*, 80(8), pp. 304-305.

* cited by examiner

*Primary Examiner*—Porfirio Nazario-Gonzalez
*Assistant Examiner*—Yate' K Cutliff
(74) *Attorney, Agent, or Firm*—Dowell $ Dowell, PC

(57) ABSTRACT

A method for preparing an ester bleach activator compound is disclosed. The method includes (A) preparing fatty acid monoester; (B) making chloroformate by reacting the fatty acid monoester with at least one selected from the group consisting of phosgene, diphosgene and triphosgene in the presence of base; and (C) reacting the chloroformate with hydroxybenzene, its derivatives, or its salts in solvent. According to the method, the ester bleach activator compound can be made in a simple and economic way.

5 Claims, No Drawings

METHOD FOR PREPARING ESTER COMPOUNDS AS BLEACH ACTIVATORS

TECHNICAL FIELD

The present invention relates to a method for preparing an ester compounds for bleach activators.

BACKGROUND ART

The bleaching method using inorganic peroxides such as sodium perborate tetrahydrate, sodium perborate monohydrate, sodium percarbonate, urea peroxohydrate, or sodium peroxide enables to remove contaminants such as stains from fruit juice, coffee, wine, or sap more effectively, i.e., stains. However, the bleaching ability of the inorganic peroxide significantly varies depending on the temperature. For example, sodium perborate shows optimum effects at higher than 80° C., and sodium percarbonate at higher than 60° C. But both are not effective in the cool water, i.e. at 20 to 25° C. in summer or at about 5° C. in winter. Thus, bleach activator method was introduced for inorganic peroxides to present comparable bleaching effects even at a low temperature.

Even though TAED (tetra acetyl ethylene diamine) is most commonly used for the purpose of activating a bleach, it is not effective in removing oily stains such as sebum. U.S. Pat. No. 4,412,934, No. 4,483,778, No. 4,606,838 and No. 4,671,891 disclose bleaching agents using acyl compound as a bleach activator, but it is not cost effective because it need to be used in plenty. And U.S. Pat. No. 4,686,061, No. 5,043,089 and EP No. 0210674 disclose a bleach activation of carbonate derivatives, but it leaves bleach odor because its molecular structure is changed in laundry water. Moreover U.S. Pat. No. 4,179,390, No. 4,259,201, No. 5,098,598, No. 5,520,844, and No. 5,575,947 disclose many organic peroxycarboxylic acids as bleach activators, but these bleach activators are unstable in heat and thus tends to lose an active oxygen of them. In order to solve such problem, a technique for coating and granulating organic peroxycarboxylic acid is introduced (see EP No. 396,341 and EP No. 256,443). However, this technique is bad with regard to economical efficiency, and decreases aqueous solubility to make the bleach activator remained in the cloth.

With the reasons above, an ester bleach activator is preferred since it is capable of releasing peroxycarboxylic acid for activating a bleach together with inorganic peroxides only in a wash water, particularly releasing peroxycarboxylic acid even at low temperature, has storage stability to make long time storage possible, shows excellent bleaching power against hydrophobic stains as well as hydrophilic stains, and rarely makes bleach odor.

U.S. Pat. No. 5,705,091 discloses such an ester bleach activator compound. However, the ester bleach activator compound is made under the conditions: 1) argon gas is used when phosgene is added for reaction, and the reaction temperature should be controlled low at about $-78°$ C., and 2) hydroxybenzene, its derivatives, or its salts are added and reacted in an organic solvent such as methylcyanide ($CH_3CN$). Thus, the above technique disadvantageously requires very complex manufacturing procedure and shows low yield as much as about 50%.

DISCLOSURE OF INVENTION

The present invention is designed to solve the problems of the prior art, and therefore an object of the present invention is to provide a method for preparing an ester compound having many advantages as a bleach activator in a simple and economic way.

In order to accomplish the above object, the present invention provides a method for preparing an ester bleach activator compound having the structure of the following Chemical Formula 1, which includes (A) preparing a fatty acid monoester; (B) making a chloroformate by reacting the fatty acid monoester with at least one selected from the group consisting of phosgene, diphosgene and triphosgene in the presence of base; and (C) reacting the chloroformate with hydroxybenzene, its derivatives, or its salts in solvent.

Chemical Formula 1

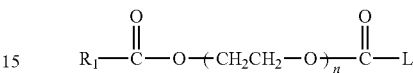

In the Chemical Formula 1, $R_1$ is a linear or branched alkyl of 1 to 19 carbon atoms, a linear or branched alkenyl of 1 to 19 carbon atoms, or a mixture of at least two selected from them, n is an integer from 1 to 10, and L is one of the following leaving groups.

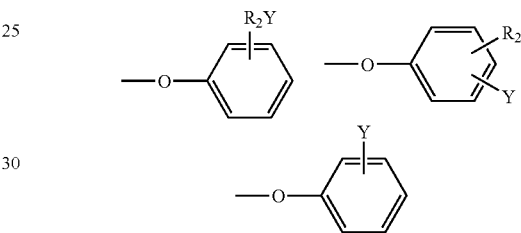

In the above leaving groups, $R_2$ is alkyl of 1 to 20 carbon atoms or alkenyl of 1 to 20 carbon atoms, Y is one selected from the group consisting of hydrogen, chlorine, bromine, $SO_3M$, $CO_2M$ and $OSO_2M$, and M is one selected from the group consisting of hydrogen, alkaline metal ions, ammonium ion and equivalent alkali earth metal ions.

In the method for preparing an ester bleach activator compound according to the present invention, the step (B) for making a chloroformate is conducted in the presence of base, and the base may be an organic or inorganic base, and specifically sodium hydroxide, potassium hydroxide, triethylamine, N,N-diisopropylethylamine and so on may be used. The reaction temperature of the step (B) is preferably kept in the range of 10 to 40° C.

In addition, in the method for preparing an ester bleach activator compound according to the present invention, the solvent of the step (C) is preferably water.

BEST MODES FOR CARRYING OUT THE INVENTION

Hereinafter, a method for preparing an ester bleach activator compound according to the present invention will be described in details.

At first, a fatty acid monoester having the structure of the following Chemical Formula 2 is prepared.

Chemical Formula 2

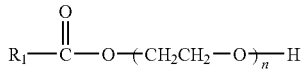

In the Chemical Formula 2, $R_1$ is a linear or branched alkyl of 1 to 19 carbon atoms, a linear or branched alkenyl of 1 to 19 carbon atoms, a mixture of at least two selected from them, and n is an integer from 1 to 10.

The compound of the Chemical Formula 2 may be obtained by means of esterification of fatty acid with ethylene glycol or ethylene oxide. In more detail, an excess of ethylene glycol or ethylene oxide is added to fatty acid and then reacted under an acid catalyst with heating at a normal pressure. Then it is esterificated with removing a generated water. A preferred amount of the added ethylene glycol or ethylene oxide is 1.0 to 10.0 equivalent weight of the fatty acid, and 0.0 to 0.5 wt % p-toluene sulfonate, sulfuric acid or hydrochloric acid on the basis of total weight may be used as the acid catalyst. The reaction temperature is preferably in the range of 60 to 150° C., and the reaction time is preferably in the range of 2 to 10 hours.

In addition to them, the compound of the Chemical Formula 2 may be obtained by reacting alkanoyl chloride compound with ethylene glycol or ethylene oxide as disclosed in U.S. Pat. No. 5,705,091, and other well-known methods may also be used.

And then, chloroformate having the structure of the following Chemical Formula 3 is made by reacting the prepared fatty acid monoester with phosgene, diphosgene or triphosgene in the presence of base.

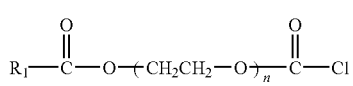

Chemical Formula 3

In the Chemical Formula 3, $R_1$ is a linear or branched alkyl of 1 to 19 carbon atoms, a linear or branched alkenyl of 1 to 19 carbon atoms, or a mixture of at least two selected from them, and n is an integer from 1 to 10.

The aforementioned chloroformate-making step is now described in more detail. The prepared fatty acid monoester and a suitable base are put into a reactor together with inorganic solvent, and then phosgene, diphosgene or triphosgene is added slowly thereto, for example, at a temperature from −10 to 10° C. The added amount of the fatty acid monoester is preferably 1.0 to 4.0 equivalent weight of the phosgene compound. Meanwhile, the base may be an organic or inorganic base, and specifically sodium hydroxide, potassium hydroxide, calcium hydroxide, triethylamine, N,N-diisopropylethylamine and so on may be used. And then, after reaction with stirring at a suitable temperature, an organic layer is separated by using water. A preferred reaction temperature is 10 to 40° C. And then, the moisture is removed by using a moisture separator such as magnesium sulfate anhydride, and the organic solvent is vacuum-distilled to make the chloroformate.

Lastly, the chloroformate made in the aforementioned way is reacted with hydroxybenzene, its derivatives, or its salts to make an ester bleach activator compound expressed by the following Chemical Formula 1.

Chemical Formula 1

In the Chemical Formula 1, $R_1$ is a linear or branched alkyl of 1 to 19 carbon atoms, a linear or branched alkenyl of 1 to 19 carbon atoms, or a mixture of at least two selected from them, n is an integer from 1 to 10, and L is one selected from the group having the structure of the following Chemical Formula 4,

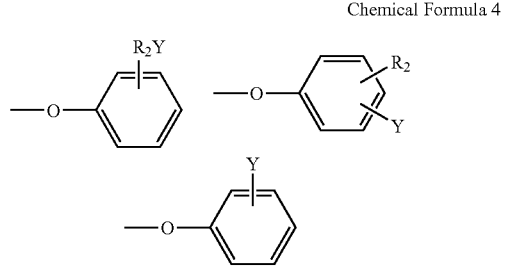

Chemical Formula 4

In the Chemical Formula 4, $R_2$ is alkyl of 1 to 20 carbon atoms or alkenyl of 1 to 20 carbon atoms, Y is one selected from the group consisting of hydrogen, chlorine, bromine, $SO_3M$, $CO_2M$ and $OSO_2M$, and M is one selected from the group consisting of hydrogen, alkaline metal ions, ammonium ion and equivalent alkali earth metal ions.

The method for making the ester bleach activator compound having the structure of the Chemical Formula 1 from the chloroformate is now described in more detail. Chloroformate and hydroxybenzene, its derivatives, or its salts are heated for reaction in a suitable solvent and then cooled to room temperature. The solvent is preferably water, and the content of the water is preferably 10 to 60 wt % on the basis of the total weight of the reaction system including the chloroformate, the water and hydroxybenzene, its derivatives, or its salts when considering facility of reaction and facility of reactant filtration. In case water is used as the solvent, suitable reaction temperature and time are respectively 20 to 100° C. and 0.1 to 5 hours. The solvent is eliminated by filtering or spraying sediment generated during the above procedure, and the final ester bleach activator compound is then obtained through a drying process.

Hereinafter, a preferred embodiment of the present invention will be described in detail. Prior to the description, it should be understood that various modifications are possible to the embodiments of the present invention, and it should be understood that the scope of the invention is not limited to the following embodiments. The embodiments are purposed to merely give better explanation of the invention to those ordinarily skilled in the art.

Embodiment (A) Preparing 2-Hydroxylethyl Decanoate 172 g (1.0 mol) of decanoic acid and an excess of 186 g (3.0 mol) ethylene glycol are put into a 4-neck flask with a stirrer, a thermometer, a condenser, and a distiller, then reacted at a normal pressure at 90° C. for 2 hours with the use of 0.4 g p-toluene sulfonate as a catalyst, and then esterificated for 2 hours at a pressure of 30 torr with eliminating water generated during the reaction. After the reaction, the reactant is analyzed to measure the acid value by means of A.O.C.S. analyzing method (Official Method Te 2a-64, 1987). A content of fatty acid is not more than 1.0%. 100 g of distilled water is added to the obtained reactant, and then stirred for 10 minutes, and then a separated lower layer is removed. And then, 150 g of distilled water is added again thereto, and then stirred for 20 minutes, and then a separated lower layer is removed again. In order to eliminate moisture contained therein, the reactant is treated for 20 minutes at 75° C. with a pressure of 30 torr, thereby making fatty acid monoester having the structure of the following Chemical Formula 5.

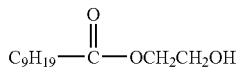
Chemical Formula 5

In the reactant, the content of the fatty acid monoester is 93% or above, the content of fatty acid is 1% or less, the content of moisture is 0.5% or less, and the content of diester is 5% or less. This reactant is applied to the following reaction for making a chloroformate as it is.

(B) Preparing 2-Chlorocarbonyl Oxyethyl Decanoate 33 g the compound (2-hydroxyethyl decanoate) of the Chemical Formula 5 prepared in the above process and 17.16 g of diphosgene are added and melted in 50 ml of methylenechloride at 0 to 4° C., and then reacted for 2 hours at room temperature in the presence of amine. Subsequently, the organic layer is separated by using water, and then moisture is eliminated by using magnesium sulfate anhydrate. And then, the solvent is removed by means of vacuum distillation, and then 41.7 g the compound of brown liquid having the structure of the following Chemical Formula 6 is obtained through the drying process.

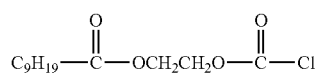
Chemical Formula 6

(C) Preparing Decanoyloxyethoxycarbonyloxybenzenesulfonate 10.55 g NaOH and 61.24 g 4-hydroxybenzenesulfonic acid sodium salt dihydrate are well dissolved at 0 to 30° C. in 120 ml of water. Then, 73.45 g of the compound (2-chlorocarbonyl oxyethyl decanoate) is added thereto, and then stirred for 2 hours at 60° C. Subsequently, it is cooled to room temperature and then filtered to remove solvent and salt, and then dried to obtain 109.43 g of white solid products having the structure of the following Chemical Formula 7.

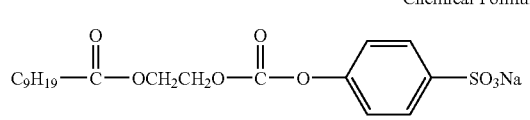
Chemical Formula 7

INDUSTRIAL APPLICABILITY

As described above, the method of the present invention is simple and economical, so it may be usefully applied to make the ester bleach activator compound expressed by the Chemical Formula 1, which has many advantages.

What is claimed is:

1. A method for preparing an ester bleach activator compound expressed by the following Chemical Formula 1, the method comprising:

(A) preparing a fatty acid monoester having the structure of the following Chemical Formula 2;

(B) making a chloroformate having the structure of the following Chemical Formula 3 by reacting the fatty acid monoester with at least one selected from the group consisting of phosgene, diphosgene and triphosgene in the presence of base; and (C) reacting the chloroformate with hydroxybenzene, its derivatives, or its salts in water,

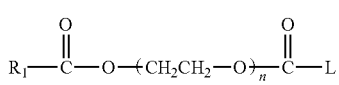
Chemical Formula 1

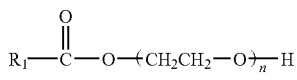
Chemical Formula 2

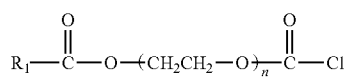
Chemical Formula 3 where, in the Chemical Formulas 1, 2 and 3, $R_1$ is a linear or branched alkyl of 1 to 19 carbon atoms, a linear or branched alkenyl of 1 to 19 carbon atoms, or a mixture of at least two selected from them, n is an integer from 1 to 10, and L is one selected from the group having the structure of the following Chemical Formula 4,

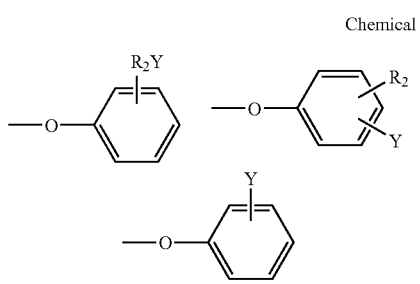
Chemical Formula 4 where, in the Chemical Formula 4, $R_2$ is alkyl of 1 to 20 carbon atoms or alkenyl of 1 to 20 carbon atoms, Y is one selected from the group consisting of hydrogen, chlorine, bromine, $SO_3M$, $CO_2M$ and $OSO_2M$, and M is one selected from the group consisting of hydrogen, alkaline metal ions, ammonium ion and equivalent alkali earth metal ions.

2. The method for preparing an ester bleach activator compound according to claim 1, wherein the fatty acid monoester of the step (A) is prepared by reacting fatty acid with ethylene glycol or ethylene oxide.

3. The method for preparing an ester bleach activator compound according to claim 1, wherein a reaction temperature of the step (B) is kept in the range of 10 to 40° C.

4. The method for preparing an ester bleach activator compound according to claim 1, wherein the content of the water weighs 10 to 60 wt % of the total amount of (1) the water, (2) an chloroformate and (3) hydroxybenzene, its derivatives or its salts.

5. The method for preparing an ester bleach activator compound according to claim 1, wherein a reaction temperature and a reaction time of the step (C) are respectively in the ranges of 20 to 100° C. and 0.1 to 5 hours.

* * * * *